:

US011060116B2

(12) United States Patent
Redford

(10) Patent No.: US 11,060,116 B2
(45) Date of Patent: *Jul. 13, 2021

(54) ECONOMIC ETHANOL FERMENTATION SUGAR STREAM, PROCESSES AND SYSTEMS OF PRODUCING SAME

(71) Applicant: POET Research, Inc., Sioux Falls, SD (US)

(72) Inventor: Steven G. Redford, Brandon, SD (US)

(73) Assignee: POET Research, Inc., Sioux Falls, SD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/255,295

(22) Filed: Jan. 23, 2019

(65) Prior Publication Data
US 2019/0153481 A1 May 23, 2019

Related U.S. Application Data

(63) Continuation of application No. 14/983,265, filed on Dec. 29, 2015, now Pat. No. 10,233,466.

(60) Provisional application No. 62/098,434, filed on Dec. 31, 2014.

(51) Int. Cl.
| C12P 7/06 | (2006.01) |
| C12M 1/00 | (2006.01) |
| C12P 19/02 | (2006.01) |

(52) U.S. Cl.
CPC ............... *C12P 7/06* (2013.01); *C12M 21/12* (2013.01); *C12P 19/02* (2013.01); *Y02E 50/10* (2013.01)

(58) Field of Classification Search
CPC ....... C12P 19/02; C12P 19/14–22; C12P 7/06; C12P 7/14; Y02E 50/10
See application file for complete search history.

(56) References Cited

U.S. PATENT DOCUMENTS

| 3,979,375 | A | 9/1976 | Rao et al. |
| 7,138,275 | B2 | 11/2006 | Kremer et al. |
| 7,303,899 | B2 * | 12/2007 | Baldwin ................ C12P 19/04 435/96 |
| 7,452,425 | B1 | 11/2008 | Langhauser |
| 9,777,303 | B2 | 10/2017 | Jakel et al. |
| 10,233,466 | B2 | 3/2019 | Redford |
| 10,480,038 | B2 | 11/2019 | Jakel et al. |
| 2004/0187863 | A1 | 9/2004 | Langhauser |
| 2006/0251762 | A1 | 11/2006 | Jansen et al. |
| 2013/0337517 | A1 | 12/2013 | Razavi-Shirazi et al. |
| 2014/0106419 | A1 | 4/2014 | Bazzana et al. |
| 2016/0201091 | A1 | 7/2016 | Redford et al. |
| 2016/0222135 | A1 | 8/2016 | Lee |
| 2018/0016602 | A1 | 1/2018 | Franko et al. |
| 2019/0284593 | A1 | 9/2019 | Jakel et al. |
| 2019/0284649 | A1 | 9/2019 | Jakel et al. |
| 2019/0309377 | A1 | 10/2019 | Jakel et al. |

FOREIGN PATENT DOCUMENTS

| WO | 2009015333 A1 | 1/2009 |
| WO | 2013180863 A1 | 12/2013 |
| WO | WO2014100685 | * 6/2014 |

OTHER PUBLICATIONS

Kwiatkowski et al. (2006) "Modeling the process and costs of fuel ethanol production by the corn dry-grind process" Industrial Crops and Products, 23:288-296.
International Search Report and Written Opinion from International Application No. PCT/US2015/067944, dated Apr. 15, 2016 (12 pages).
International Search Report and Written Opinion from International Application No. PCT/US2015/067951, which is the PCT counterpart of U.S. Appl. No. 14/983,320, dated Apr. 20, 2016, (11 pages).
Dien et al., "The U.S. corn ethanol industry: An overview of current technology and future prospects", Int. Sugar Jnl. vol. 104, No. 1241, pp. 204-211, 2002, (8 pages).
Ezeji et al., "Production of acetone-butanol-ethanol (ABE) in a continuous flow bioreactor using degermed corn and Clostridium beijerinckii", Process Biochemistry, vol. 42, pp. 34-39, 2007, (6 pages).
Jessen, "The Quest for Maximu Yield: Wet Mill to Dry Mill", Ethanol Producer Magazine, pp. 1-2, Aug. 15, 2011, (2 pages).
Kim et al., "Compostion of corn dry-grind ethanol by-products: DDGS, wet cake, and thin stillage", Bioresource Technology, vol. 99, pp. 5165-5176, 2008, (12 pages).
Mueller et al., "2012 Corn Ethanol: Emerging Plant Energy and Environmental Technologies", University of Illinois at Chicago, Energy Resources Center, College of Engineering, pp. 1-31, Apr. 29, 2013, (31 pages).
Sigma Aldrich Chemicals—Technical Library, "Particle Size Conversion Table", retrieved from https://www.sigmaaldrich.com/chemistry/stockroom-reagents/learning-center/technical-library/particle-size-conversion.html, available on 2009, (1 page).
Taylor et al., "Dry-Grind Process for Fuel Ethanol by Continuous Fermentation and Stripping", Biotechnology Progress, vol. 16, No. 4, pp. 541-547, 2000, (7 pages).
Wang et al., "Effect of Endosperm Hardness on an Ethanol Process Using a Granular Starch Hydrolyzing Enzyme", American Society of Agriculture and Biological Engineers, vol. 53, ISSN. 2151-0032, pp. 307-312, 2010, (6 pages).

(Continued)

*Primary Examiner* — Thane Underdahl
(74) *Attorney, Agent, or Firm* — Kagan Binder, PLLC

(57) ABSTRACT

Methods and system for producing a slip stream of sugar, for example for use in the production of one or more chemicals, in ethanol fermentation facilities. In some embodiments, the methods and systems have little to no impact on the level of production of ethanol, despite also producing a slip stream of sugar. The methods and systems can be implemented in dry mill ethanol, wet mill ethanol, and lignocellulosic ethanol fermentation facilities and processes.

22 Claims, No Drawings

(56) References Cited

OTHER PUBLICATIONS

Jakel, "Product Diversification: Proven Path Forward", Presented at American Coalition for Ethanol Annual Conference, Omaha, NE, Aug. 2017, https://ethanol.org/news/news/2017/08, (71 pages).
Robert, "Industrial Glucose: Bridging the Biochemical GAP", Presented at ABLC2019, Renewable Chemicals Summit, Washington, DC, Apr. 4, 2019, (20 pages).
Unpublished Utility U.S. Appl. No. 17/009,456, filed Sep. 1, 2020.

\* cited by examiner

ECONOMIC ETHANOL FERMENTATION SUGAR STREAM, PROCESSES AND SYSTEMS OF PRODUCING SAME

CROSS-REFERENCE TO RELATED APPLICATIONS

This application is a continuation of U.S. patent application Ser. No. 14/983,265, filed Dec. 29, 2015, entitled, "Economic Ethanol Fermentation Sugar Stream, Processes and Systems of Producing Same", which claims the benefit of U.S. Provisional Patent Application No. 62/098,434, entitled, "Economic Ethanol Fermentation Sugar Stream, Processes and Systems of Producing Same," and having a filing date of Dec. 31, 2014, the entire contents of each application are incorporated herein by reference.

FIELD

The specification relates to methods and systems for producing sugar in ethanol fermentation facilities. The specification also relates to methods and systems for simultaneously producing ethanol and a slip stream of sugar, for example for the production of non-ethanol chemicals in ethanol fermentation facilities with little to no impact on the ethanol facility's alcohol yield.

BACKGROUND

First generation ethanol fermentation facilities produce ethanol from starch-based feedstock such as corn. In a typical conventional corn-to-ethanol fermentation process, starch present in corn is broken down into simple sugars, which can be fermented by an ethanologen such as yeast into ethanol.

Traditional ethanol production processes typically involve five basic steps: milling, cooking, saccharification, fermentation, distillation and recovery. In some such processes, the milling step is a dry milling step in which corn is ground into flour. Cooking may involve mixing the flour with water to form a slurry, heating the slurry to above the gelatinization temperature of the corn, and treating the slurry with a liquefying enzyme to hydrolyze starch contained therein to dextrins. In the saccharification step, enzymes are added to the mash to convert the corn starch into simple sugars. The fermentation of the sugars by an ethanologen such as yeast produces a beer, which is separated into ethanol and whole stillage by distillation. The whole stillage may be subject to further processing wherein it is separated into wet cake and thin stillage. The thin stillage passes through evaporators to produce a syrup, which may be recombined and dried with the wet cake to produce distillers grains with solubles (DDGS), an animal feed. Not all dry mill ethanol production processes involve all the identified steps. For example, in some dry mill ethanol production processes, saccharification and fermentation are not independent steps but occur simultaneously. As another example, some dry mill ethanol production processes do not involve liquefaction. As yet another example, POET®'s BPX® hydrolysis process does not use a jet cooker (i.e. a cooking step).

In order to produce a pure sugar stream while also making other components of corn available to sell, some conventional processes use a wet mill rather than dry mill approach. In wet milling, corn is soaked in water to soften the grain and facilitate separating the various components of the corn kernel. After "steeping", various components such as starch, fiber and germ are separated from one another for separate processing into a variety of products. Fractionation equipment, however, is expensive and increases the cost of producing the sugar stream.

SUMMARY

The present disclosure relates in part to methods and systems for simultaneously producing a slip stream of sugar stream, for example for the production of non-ethanol chemicals, as well as a sugar stream for the production of ethanol in ethanol fermentation facilities while essentially maintaining the same ethanol titer as could be produced by the same facility if it did not produce the biochemical sugar stream.

In some such embodiments, the methods involve producing a slip stream of sugar in an ethanol fermentation facility configured to produce a desired ethanol titer by preparing a fermentable stream from an amount of feedstock, removing a first portion of the fermentable stream prior to fermentation by an ethanologen, and producing ethanol from the second, remaining portion of the fermentable stream consistent with the desired ethanol titer. In some embodiments, the first portion is removed after saccharification of the fermentable stream. In some embodiments, the first portion is removed prior to saccharification of the fermentable stream.

In some embodiments, the methods are implemented in a first generation (starch-based) ethanol fermentation facility and the fermentable stream is a slurry or a mash. In some further embodiments, wherein the fermentable stream is a mash, the mash is processed to remove solids and produce a sugar stream. The first generation process may be any process for converting starch-based materials such as corn into ethanol, for example including both processes which include and do not include a cooking step. In yet further embodiments, the removed solids are returned to the second portion of the fermentable stream (i.e. mash). In further embodiments, the sugar stream is also processed, for example the sugar stream is filtered using a membrane, to remove enzymes and the removed enzymes are recycled into the second portion of the fermentable stream (i.e. mash).

In other further embodiments, wherein the fermentable stream is a slurry, both the first portion of the slurry is processed into a first mash and the second portion of the slurry is processed as per usual into a second mash. In certain further embodiments, the first mash is further processed to remove solids and produce a sugar stream. In yet further embodiments, the removed solids are combined with the second mash. In further embodiments, the sugar stream is also processed, for example the sugar stream is filtered using a membrane, to remove enzymes and the removed enzymes are recycled into the second portion of the fermentable stream (i.e. mash).

In some embodiments, the process is implemented in a lignocellulosic (also referred to as cellulosic) ethanol fermentation facility. In further embodiments, the fermentable stream is removed before saccharification. In other further embodiments, the fermentable stream is a saccharified liquor and therefore the fermentable stream is removed after saccharification. In some embodiments, the fermentable stream, for example the saccharified liquor, is further processed to produce a sugar stream.

In certain embodiments the desired ethanol titer is approximately the ethanol-producing facility's maximum titer. For example, in certain embodiments, an amount of feedstock is used which generates a fermentable stream (e.g.

mash) from which both a first portion for production of non-ethanol chemicals and a second portion for production of ethanol are derived, wherein the second portion is capable of producing the maximum titer of ethanol independently of the first portion. As another example, an amount of feedstock is used which produces a fermentable stream that if fermented without separation into a first portion for production of non-ethanol chemicals and second portion for production of ethanol would result in an ethanol titer in excess of what the fermentation facility's ethanologen can tolerate. In some embodiments, the amount of feedstock ranges from an amount that would produce an ethanol titer that is too high for the ethanologen to tolerate if both the first fermentable stream (e.g. mash) and second fermentable stream (e.g. mash) could be fermented in the same tank volume to an amount of feedstock consistent with the ethanol fermentation facility's capability.

In some embodiments, the systems comprise an ethanol fermentation facility configured to produce a desired titer of ethanol, and componentry configured to remove a slip stream from a fermentable stream produced in the facility with essentially little or no impact to the desired ethanol titer production. In some embodiments, the componentry is configured to remove the slip stream after saccharification. In some embodiments the componentry is configured to remove the slip stream before saccharification. In some embodiments the systems further comprise componentry to separate and/or return solids derived from the slip stream back to the ethanol facility, for example back to a mash or a saccharified liquor produced in the facility. In further embodiments, the systems further comprise componentry to separate residual enzymes from the sugar stream after removal of solids and return the enzymes back to the ethanol facility. In some embodiments, the facility is a starch-based ethanol facility. In some embodiments, the facility is a dry mill starch-based ethanol facility. In some embodiments, the facility is a dry mill corn-to-ethanol facility. In some embodiments, the facility is a lignocellulosic ethanol facility.

The identified embodiments are exemplary only and are therefore non-limiting. The details of one or more non-limiting embodiments according to the disclosure are set forth in the descriptions below. Other embodiments according to the disclosure should be apparent to those of ordinary skill in the art after consideration of the present disclosure. For example, although implementations of the processes and systems are primarily described herein with reference to dry mill ethanol production processes and systems, they may be adapted to wet mill ethanol processes and systems, as well as lignocellulosic ethanol processes and systems as a person of skill in the art would readily understand from reading this specification. Similarly, although implementations of the processes and systems primarily refer to corn-to-ethanol fermentation processes and systems, they may be adapted to other biomass-to-ethanol fermentation processes and systems, again as a person of skill could understand from reading this specification.

DETAILED DESCRIPTION

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrases "for example," "such as," "including" and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common United States patent law definition of "comprising" and is therefore interpreted to be an open term meaning "at least the following" and also interpreted not to exclude additional features, limitations, aspects, etc.

The term "about" is meant to account for variations due to experimental error or to permit deviations from the measurements that don't negatively impact the intended purpose. All measurements or numbers are implicitly understood to be modified by the word about, even if the measurement or number is not explicitly modified by the word about.

The term "substantially" is meant to permit deviations from the descriptive term that don't negatively impact the intended purpose. All descriptive terms are implicitly understood to be modified by the word substantially, even if the descriptive term is not explicitly modified by the word substantially.

Where ever the terms "a" or "an" are used, "one or more" is understood unless explicitly stated otherwise or such interpretation is nonsensical in context.

The phrases: "essentially maintaining the same ethanol titer"; "with little or no impact to the ethanol facility's alcohol yield"; "consistent with the desired ethanol titer" and the like imply that for a given ethanol facility implementing a slip stream sugar process according to this disclosure any resulting reduction of ethanol production is commercially acceptable. For example, the difference in ethanol titer between a facility producing ethanol and a slip stream of sugar according to this disclosure and the same ethanol facility producing ethanol without the slip stream of sugar may be about 10%, or about 5%, or about 2%, or about 0%.

"Mash" refers to a composition comprising sugar produced in a starch-based facility. "Saccharified liquor" refers to a composition comprising sugar produced in a lignocellulosic ethanol facility. "Slurry" refers to a starch composition produced in a starch-based facility.

The phrase "sugar stream" refers to a composition that comprises sugar; a sugar stream is not necessarily pure sugar, but may be for example a mash or a purified mash (such as a mash that has been processed to remove at least a portion of solids). "Sugar stream" also refers to a stream which is diverted from an ethanol fermentation facility to provide a second source of sugar distinct from the main source of sugar which will be used to produce ethanol. Sugar in the sugar stream may be used, for example, to produce one or more chemicals.

The phrases: "removing solids from the first portion of the fermentable stream" and "removing enzymes from the sugar stream" as well as other similar phrases suggesting a purification or separation process do not require complete removal/separation/purification.

The present disclosure relates to methods and systems for producing a sugar stream, for example for use in production of non-ethanol chemicals, while also producing ethanol in a feedstock-to-ethanol fermentation process. In some embodiments, the present disclosure provides methods and systems for producing a sugar stream, for example for use in production of non-ethanol chemicals, while simultaneously maintaining ethanol production at a commercially-acceptable level, for example at essentially maximum titer levels according to the implementing ethanol fermentation facility's capability.

Ethanol fermentation processes generally involve producing a fermentable stream from a feedstock (for example a grain-based starch feedstock including whole cereal such as corn, wheat, sorghum, bulgur, barley) and thereafter producing ethanol from the fermentable stream. For example, in a starch-based ethanol fermentation process, the fermentable stream may be a mash, and producing ethanol involves fermenting sugar in the mash into ethanol. As another starch-based example, the fermentable stream may be a slurry, which is saccharified to produce a mash. The sugar in the mash is thereafter fermented into ethanol. As yet another example, in a lignocellulosic ethanol fermentation process, the fermentable stream may be a saccharified liquor, and producing ethanol involves fermenting sugar in the saccharified liquor into ethanol.

In some embodiments, methods described herein generally involve producing a fermentable stream in excess of what the implementing facility typically handles or is capable of handling, producing a slip stream of sugar from the excess fermentable stream, and producing ethanol from the remaining fermentable stream. In general, the methods involve preparing a fermentable stream from an amount of feedstock, removing a first portion of the fermentable stream prior to fermentation by an ethanologen, and producing ethanol from a second portion of the fermentable stream consistent with the desired ethanol titer.

In some embodiments, the first portion (of the fermentable stream) is removed after saccharification of the fermentable feed stream. In some such embodiments, this sugar slip stream (removed first portion) may be further purified by removing solids according to any appropriate method, such as any method known to those of ordinary skill in the art. In further embodiments, the removed solids are returned to the ethanol fermentation facility and may be recombined with the second portion of the fermentation stream or a stream derived from the second portion. In yet further embodiments, the resultant sugar stream is also subjected to a purification process targeted to remove residual enzymes. In some such embodiments, the removed residual enzymes are returned for re-use in the ethanol fermentation facility, such as recombined with the second portion of the fermentation stream or other stream derived from the second portion.

In some embodiments, the first portion of the fermentable stream is removed before saccharification of the fermentable stream. In some such embodiments, the first portion is further processed to produce sugar (such as by being subjected to a saccharification process), and the resultant sugar slip stream may be further purified, for example to remove solids. In further embodiments, the removed solids may be recombined with the second portion of the fermentation stream or a stream derived from the second portion.

In some embodiments, the desired ethanol titer is a commercially-acceptable titer. In some embodiments, the desired ethanol titer is the ethanol producing-facility's maximum ethanol titer. Accordingly, in some embodiments, the amount of feedstock is chosen to produce the desired ethanol titer that is in excess of the implementing ethanol-producing facility's capability if both the first portion of the fermentable stream and second portion of the fermentable stream could both be fermented in the same tank. In some embodiments, the amount of feedstock is chosen such that the second portion of the fermentable stream produces the desired ethanol titer. In some such embodiments, the resultant ethanol titer is a commercially-acceptable titer; in other such embodiments, the resultant ethanol titer is the ethanol facility's maximum operational ethanol titer. In some embodiments, the amount of feedstock is chosen to produce an ethanol titer that is greater than the ethanologen can tolerate, if both the first portion and second portion of the fermentable stream could be fermented in the same tank. In some embodiments, the chosen amount of feedstock may range from an amount that produces an ethanol titer greater than the ethanologen can tolerate to an amount that is greater than the implementing facility's capability. The chosen amount of feedstock may be limited by a given facility's operational parameters; a person of ordinary skill could determine the limit based on this specification and knowledge of the operations of the implementing facility.

In some embodiments, the methods may be implemented in first generation (e.g. starch-based) ethanol fermentation processes, such as a dry mill ethanol fermentation process. In other words, the "implementing facility" mentioned throughout may be a first generation ethanol fermentation facility, including facilities which use cooking steps and which do not use cooking steps in their hydrolysis process. A dry mill corn ethanol process typically involves: milling corn; slurring the corn with water; steam exploding the solids; liquefying/saccharifying the stream with enzymes; fermenting the mash; distilling the alcohol from the beer; separating the solids form the whole stillage to create wet cake; evaporating some of the water from the thin stillage to create syrup; removal of oil from the syrup; and, drying the wet cake and the syrup. However, the processes described herein are not limited in application to this typical process but may be applied to all dry mill processes including, for example, dry mill processes which do not use steam explosion or other cooking steps. In general, ethanol plants are designed to operate as efficiently as possible, i.e. to produce as high an ethanol titer as is possible. Dry mill plants typically produce titers ranging from about 12% to about 20%. Obstacles limiting the titer include the ethanologen used to ferment the sugars, and non-fermentable components ("inerts") produced in the overall process. For example, the ethanologen may not be able to tolerate higher titer, and the presence of a certain level of inerts may impact the yield of alcohol.

In order to produce a stream of sugar while still maintaining the ethanol titer, methods according to the present disclosure mill an increased amount of feedstock relative to the typical amount of feedstock used as input in a given dry mill ethanol fermentation facility process, and thereby increase the amount of sugar produced in the mash relative to the amount of sugar produced if the plant were only producing a sugar stream for ethanol. For example, in some dry mill embodiments, the amount of feedstock is chosen to produce an ethanol titer that is in excess of the maximum titer of the given ethanol fermentation facility. For example the amount of feedstock is chosen such that only a portion of the fermentation stream produced from the feedstock is required to produce the maximum ethanol titer for the given ethanol fermentation facility. In other dry mill embodiments, the amount of feedstock is chosen to produce an ethanol titer and/or inerts that is greater than the ethanologen can tolerate. In some dry mill embodiments, the amount of feedstock ranges from an amount that would produce an ethanol titer that is too high for the ethanologen to an amount of feedstock consistent with the ethanol fermentation facility's capability. In some dry mill embodiments, the amount of feedstock may be augmented above the limits described above by removing one or more components from the feedstock, such as removing fiber from the corn, thereby decreasing the level of inerts entering the fermenter per given amount of feedstock and allowing for greater grind and sugar removal. In some embodiments, the removed feedstock components are introduced back into the system at an appropriate location, such as providing removed corn fiber to the DDGS.

The additional grind results in a larger portion of fermentable stream, which in some embodiments would produce sugar that exceeds the fermentation facility's processing capability (such as by creating ethanol titers that are too high for the ethanologen to tolerate, or such as by producing an amount of inerts that impacts ethanol yield beyond what is commercially acceptable). Accordingly, a portion of the fermentable stream is removed prior to fermentation.

In some embodiments, therefore, a first portion of the fermentable stream is removed, for example for the purpose of providing a slip stream of sugar for non-ethanol chemical(s) rather than ethanol production, and the second, remaining portion may be fermented into ethanol. In some embodiments, the first portion of mash is removed after saccharification. In some dry mill embodiments, the first portion of the fermentable stream is removed after saccharification. Such methods may involve producing a slip stream of sugar in an ethanol fermentation facility configured to produce a desired ethanol titer by preparing a mash from an amount of feedstock, removing a first portion of the mash prior to fermentation by an ethanologen, which corresponds to the slip stream of sugar, and producing ethanol from the second, remaining portion of the mash consistent with the desired ethanol titer.

In other dry mill embodiments, the first portion of the fermentable stream is removed before saccharification. Such methods may involve producing a slip stream of sugar in an ethanol fermentation facility configured to produce a desired ethanol titer by a preparing a slurry from an amount of feedstock, removing a first portion of the slurry, processing the first portion of the slurry to produce a sugar stream (for example directing the slurry to a liquefaction and/or saccharification process), and producing ethanol from the second, remaining portion of the slurry consistent with the desired ethanol.

The removed mash (whether removed directly as the fermentable stream or generated from the removed fermentable stream) may be processed according to any method to generate a purified sugar slip stream. For example, the removed mash may be processed to separate out solids present in the mash, resulting in a sugar slip stream. The sugar slip stream may serve as a source of sugar for production of one or more chemicals. In some embodiments, the separated solids may be combined with the mash which is to be fermented to produce ethanol for processing and recovery in the usual course of the facility's operation. In such embodiments, the level of non-fermentable material ("inerts") that the fermentation process can handle to maintain desired efficiencies of the ethanol process will control the amount of sugar that can be produced for the chemical sugar slip stream and in turn the amount of additional input feedstock that may be used over and above what is used during usual operation of the facility (i.e. when the facility is operating to only produce a sugar stream for ethanol production).

In some embodiments, in addition to recycling solids from the first portion of the fermentable stream, enzymes in the sugar stream are also recycled into the ethanol fermentation process. For example, after solids are removed, the resultant sugar stream may be subjected to a filtration process to remove enzymes. In some embodiments, recycling enzymes into the fermentation process from the removed solids and/or from the sugar stream provides an economic benefit in that fewer enzymes need to be used in the ethanol fermentation process. To illustrate the point, if: 100% of the enzymes in the slip stream could be recycled; and if the combined volume of the first portion and second portion represents 100% of the fermentable volume, with the first portion being 20% of the total fermentable volume and the second portion representing 80% of the total fermentable volume; then only a quantity of enzymes needed for 60% of the total fermentable volume needs to be added to the second portion because the remaining amount of required enzyme may be recycled into the second portion from the first portion.

In any of the above-described embodiments, the portion of fermentable stream removed may be chosen such that the remaining portion of fermentable stream is typical of the amount of fermentable stream processed by the given fermentation facility to achieve its desired (for example maximum) ethanol titer. That is, an amount of sugar may be removed (directly by removing a portion of the mash or indirectly by removing a portion of slurry) to maintain the same amount of sugar for the given facility's typical ethanol production and consequently ethanol titer.

In some dry mill embodiments, up to about 25% by volume of the fermentable stream (e.g. mash) may be removed prior to fermentation. In some dry mill embodiments, up to about 15% by volume of the fermentable stream (e.g. mash) may be removed prior to fermentation. In some dry mill embodiments, up to about 10% by volume of the fermentable stream (e.g. mash) may be removed prior to fermentation. In some dry mill embodiments, up to about 5% by volume of the fermentable stream (e.g. mash) may be removed prior to fermentation. In some dry mill embodiments, from about 10% to about 15% by volume of the fermentable stream (e.g. mash) may be removed prior to fermentation. In some dry mill embodiments, from about 8% to about 10% by volume of the fermentable stream (e.g. mash) may be removed prior to fermentation. In some dry mill embodiments, from about 2% to about 5% by volume of the fermentable stream (e.g. mash) may be removed prior to fermentation.

In general, the upper limit of additional fermentable stream (e.g. mash) that may be produced and accordingly the upper limit of fermentable stream (e.g. mash) that may be removed relates to a given facility's processing parameters. For example, facilities that operate at lower titers may generally be able to grind more and therefore remove more fermentable stream (e.g. mash) relative facilities that operate at higher titer. The amount of additional fermentable stream (e.g. mash) that may be provided to the fermenter also depends on the chosen ethanologen and the level of inerts and/or titer it can tolerate. The amount of fermentable stream (e.g. mash) that may be removed also depends on ethanol loss that is acceptable to a given facility. For example, if a facility can accept a 10% loss in ethanol, it can remove larger amounts of sugar relative to a facility that desires to maintain its ethanol yield. As another example, if the facility can accept little to no loss in ethanol and the facility is operating at high titer, it may only be able to remove a small amount of fermentable stream (e.g. mash) by over grinding.

In some dry mill embodiments, the amount of feedstock may exceed the above guidelines if one or more components of the feedstock is removed in advance of fermentation, for example in advance of introducing the feedstock into the process or for example in advance of liquefaction, thereby decreasing the inerts that come into the fermenter permitting a greater grind and mash/sugar removal. As an example, the feedstock may be corn, and the removed component may be fiber. In some embodiments, the removed component or components, such as fiber, is/are sent directly to the Dried Distillers Grain ("DDG"). For example, in some such embodiments wherein components of the feedstock are removed upfront, up to about 37%, or up to about 40% by volume of the fermentable stream may be removed prior to fermentation.

The present disclosure also provides systems for producing a slip stream of sugar. The systems include an ethanol fermentation facility and componentry configured to remove a slip stream from a fermentation stream produced in the facility with essentially no impact to the desired ethanol titer production. In some embodiments, the ethanol facility is configured to produce ethanol from a whole cereal, such as corn. In some embodiments, the ethanol facility is configured to produce ethanol from lignocellulosic biomass. In some embodiments, the componentry is configured to remove the slip stream after saccharification of the fermentable stream. In some embodiments the componentry is configured to remove the slip stream before saccharification of the fermentable stream. In some embodiments, the system provides processing equipment for purifying the slip stream and returning components removed from the slip stream (such as solids removed from mash) back into the stream for production of ethanol (such as back into the mash in a starch-based facility or back into the saccharified liquor in a lignocelllulosic facility). In some embodiments, wherein the fermentable stream is removed prior to saccharification, the system also includes componentry for further processing of the stream to produce sugar.

A number of embodiments have been described but a person of skill understands that still other embodiments are encompassed by this disclosure. It will be appreciated by those skilled in the art that changes could be made to the embodiments described above without departing from the broad inventive concepts thereof. For example, although the process is described primarily with respect to dry mill processes, it could also be adapted to wet mill processes. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention. Methods and devices within the scope of the disclosure can also be defined in accordance with the below embodiments.

Non-inclusive additional embodiments:
1. A process for producing a slip stream of sugar implemented in an ethanol-producing fermentation facility configured to produce a desired ethanol titer, comprising:
   a. preparing a fermentable stream from an amount of feedstock;
   b. removing a first portion of the fermentable stream prior to fermentation by an ethanologen; and,
   c. producing ethanol from a second portion of the fermentable stream consistent with the desired ethanol titer.
2. A process according to embodiment 1, wherein the desired ethanol titer is approximately the ethanol-producing facility's maximum titer.
3. A process according to embodiment 1 or embodiment 2, further comprising: separating solids from the first portion of the fermentable stream and providing the solids at least to the second portion of the fermentable stream to produce a total amount of solids in the second portion.
4. A process according to embodiment 1 or embodiment 2, wherein the amount of feedstock is chosen to produce an ethanol titer that is in excess of the maximum titer of the ethanol-producing facility, if both the first portion and second portion of the fermentable stream were fermented.
5. A process according to embodiment 1 or embodiment 2, wherein the amount of feedstock is chosen to produce an ethanol titer that is greater than the ethanologen can tolerate, if both the first portion and second portion of the fermentable stream were fermented.
6. A process according to embodiment 3, wherein the total amount of solids in the second portion does not negatively impact the desired ethanol titer.
7. A process according to embodiment 3, wherein the process maintains the desired ethanol titer.
8. A process according to any of embodiments 1-7, wherein the fermentable stream is chosen from a slurry, a mash, and a saccharified liquor.
9. A process according to embodiment 8, wherein the process is implemented in a starch-based ethanol fermentation facility and the fermentable stream is a slurry or a mash.
10. A process according to embodiment 9, wherein the first portion is removed after saccharification and the fermentable stream is a mash.
11. A process according to embodiment 9, wherein the first portion is removed before saccharification and the fermentable stream is a slurry.
12. A process according to embodiment 10 or embodiment 11, wherein the feedstock is a whole cereal.
13. A process according to embodiment 12, wherein the feedstock is corn.
14. A process according to any of embodiments 6,7, and 9-12, wherein the process is implemented in a starch-based ethanol fermentation facility and comprises:
   a. milling the feedstock;
   b. cooking the milled feedstock, wherein cooking comprises mixing the milled feedstock to form a slurry and hydrolyzing the slurried feedstock to produce dextrins; and, if necessary,
   c. saccharifying the dextrins to produce glucose.
15. A process according to embodiment 14, wherein the feedstock has a gelatinazation temperature and hydrolysis is performed above the gelatinization temperature of the feedstock.
16. A process according to embodiment 14, further comprising fractionating the feedstock.
17. A process according to any of embodiments 1-10 and 12-16, further comprising separating sugar from the first portion of the fermentable stream.
18. A process according to embodiment 17, further comprising using the sugar to produce one or more chemicals.
19. A process according to any of embodiments 1-9 and 11-16, further comprising directing the first portion to a liquefaction process, saccharification process or both to produce a mash; and processing the mash to produce a sugar stream.
20. A process according to embodiment 19, wherein the sugar stream derived from the first portion is used to produce one or more chemicals.

21. A system for producing a slip stream of sugar, comprising:
   a. an ethanol fermentation facility configured to produce a desired titer of ethanol from a whole cereal;
   b. componentry configured to remove a slip stream from a fermentable stream produced in the facility with essentially no impact to the desired ethanol titer production.
22. A system according to embodiment 21, wherein the desired ethanol titer is approximately the ethanol fermentation facility's maximum titer.
23. A system according to embodiments 21 or 22, wherein the componentry is configured to remove the slip stream after saccharification.
24. A system according to embodiments 21 or 22, wherein the componentry is configured to remove the slip stream before saccharification.
25. A system according to any of embodiments 21-24 further comprising componentry configured to return solids derived from the slip stream back to a mash or saccharified liquor produced in the facility.

What is claimed is:

1. A process for an ethanol fermentation facility, the process comprising:
   (i) providing a ground grain feedstock;
   (ii) saccharifying the ground grain feedstock to produce a sugar composition comprising monosaccharide sugars and solids;
   (iii) dividing the sugar composition into a first sugar stream comprising monosaccharide sugars from the sugar composition and a second sugar stream comprising monosaccharide sugars and solids from the sugar composition;
   (iv) providing the first sugar stream to a chemical production first process; and
   (v) providing the second sugar stream to a chemical production second process, different from the chemical production first process, comprising:
      (a) fermenting the second sugar stream to produce a beer; and
      (b) recovering ethanol and solids from the beer.
2. The process according to claim 1, wherein the grain is a whole cereal.
3. The process according to claim 2, wherein the whole cereal is corn.
4. The process according to claim 3, further comprising fractionating the corn.
5. The process according to claim 1, wherein the second sugar stream produces up to a maximum ethanol titer compared to the same ethanol facility producing ethanol without the chemical production first process.
6. The process according to claim 1, wherein the amount of ground grain feedstock is chosen to produce an ethanol titer that is greater than an ethanologen can tolerate, if both the first sugar stream and the second sugar stream were fermented together to produce ethanol.
7. The process according to claim 1 further comprising separating solids from the first sugar stream and introducing the separated solids into the chemical production second process.
8. The process of claim 7, further comprising introducing the separated solids into the fermenting step of the chemical production second process.
9. The process according to claim 7, wherein introducing the solids into the chemical production second process results in a total amount of solids in the chemical production second process that does not negatively impact an ethanol titer.
10. The process according to claim 7, wherein the separated solids are introduced into the chemical production second process before fermenting the second sugar stream.
11. The process according to claim 1 further comprising separating solids from the first sugar stream.
12. The process of claim 1, wherein the recovered ethanol comprises no less than 10% of an ethanol titer compared to the same ethanol facility producing ethanol without the chemical production first process.
13. The process of claim 1, further comprising separating solids from the first sugar stream and introducing the solids into the chemical production second process after fermenting the second sugar stream.
14. The process according to claim 13, wherein the solids comprise corn fiber and wherein introducing the solids into the chemical production second process after fermenting the second sugar stream comprises introducing the solids to dried distiller's grain.
15. The process according to claim 13, wherein the solids comprise corn fiber and wherein recovering solids from the beer comprises separating the solids from whole stillage to form wet cake.
16. The process of claim 1, wherein the first sugar stream comprises enzymes and further comprising removing enzymes from the first sugar stream and recycling the removed enzymes into the chemical production second process.
17. The process according to claim 1 further comprising filtering the sugar composition to provide the first sugar stream.
18. The process according to claim 17, wherein the first sugar stream comprises enzymes and further comprising filtering the first sugar stream to remove enzymes.
19. The process according to claim 1, wherein the separated solids comprise fiber.
20. A process for an ethanol fermentation facility, the process comprising:
   (i) providing a ground grain feedstock;
   (ii) saccharifying the ground grain feedstock to produce a sugar composition comprising monosaccharide sugars and solids;
   (iii) separating the sugar composition into a first sugar stream comprising monosaccharide sugars from the sugar composition and a second sugar stream comprising monosaccharide sugars and solids from the sugar composition, wherein separating the sugar composition comprises separating solids from the sugar composition into the second sugar stream;
   (iv) providing the first sugar stream to a chemical production first process; and
   (v) providing the second sugar stream to a chemical production second process, different from the chemical production first process, comprising:
      (a) fermenting the second sugar stream to produce a beer; and
      (b) recovering ethanol from the beer.
21. The process of claim 20, wherein the first sugar stream comprises enzymes and further comprising removing enzymes from the first sugar stream and recycling the removed enzymes into the chemical production second process.
22. The process according to claim 21, wherein the first sugar stream comprises enzymes and wherein removing enzymes comprises filtering the first sugar stream to remove enzymes.

* * * * *